US012799022B2

(12) United States Patent
Li et al.

(10) Patent No.: US 12,799,022 B2
(45) Date of Patent: Nov. 17, 2026

(54) GLASS CERAMIC MATERIAL, METHOD FOR PREPARING THE SAME, AND DENTURE

(71) Applicant: SHENZHEN YURUCHENG DENTAL MATERIALS CO., LTD., Shenzhen (CN)

(72) Inventors: Zongyu Li, Shenzhen (CN); Wei Liu, Shenzhen (CN); Jian Wang, Shenzhen (CN); Jianjun Liu, Shenzhen (CN)

(73) Assignee: SHENZHEN YURUCHENG DENTAL MATERIALS CO., LTD., Shenzhen (CN)

( * ) Notice: Subject to any disclaimer, the term of this patent is extended or adjusted under 35 U.S.C. 154(b) by 543 days.

(21) Appl. No.: 18/474,573

(22) Filed: Sep. 26, 2023

(65) Prior Publication Data

US 2024/0132395 A1 Apr. 25, 2024
US 2024/0228365 A9 Jul. 11, 2024

(30) Foreign Application Priority Data

Oct. 19, 2022 (CN) ......................... 202211280088.8

(51) Int. Cl.
*C03C 10/00* (2006.01)
*A61C 13/00* (2006.01)
(Continued)

(52) U.S. Cl.
CPC ...... *C03C 10/0009* (2013.01); *A61C 13/0006* (2013.01); *A61C 13/083* (2013.01);
(Continued)

(58) Field of Classification Search
CPC ... C03C 10/0009; C03C 4/0021; C03B 19/06; C03B 32/02; A61K 6/833; A61C 13/0006; A61C 13/083
See application file for complete search history.

(56) References Cited

U.S. PATENT DOCUMENTS

2016/0236971 A1 8/2016 Rampf et al.
2020/0317561 A1 10/2020 Arnold et al.

FOREIGN PATENT DOCUMENTS

CN 101407375 B 12/2010
CN 104108883 A 10/2014
(Continued)

OTHER PUBLICATIONS

Translation for CN 113264684, Aug. 17, 2021.*
(Continued)

*Primary Examiner* — C Melissa Koslow
(74) *Attorney, Agent, or Firm* — Westbridge IP LLC

(57) ABSTRACT

Disclosed are a glass ceramic material, a preparation method thereof, and a denture. The glass ceramic material includes the following components by mass percentage: 58% to 72% of $SiO_2$, 0% to 4% of $Al_2O_3$, 0% to 5% of $Na_2O$, 3% to 8% of $K_2O$, 8% to 17% of $Li_2O$, 2.5% to 5% of $P_2O_5$, 0% to 2% of MgO, 0% to 2.5% of $B_2O_3$, 0% to 5% of ZnO and 0% to 3% of $ZrO_2$. In the present application, by optimizing the composition and ratio of the glass ceramic material, and combining with a matching process system, it is possible to control the formation of lithium disilicate while the crystallinity of lithium metasilicate glass ceramic can be improved without an introduction of a high ratio of zirconia content, thereby improving the grinding performance of the glass ceramic. The present application is applicable to the field of material technology.

6 Claims, 2 Drawing Sheets

(51) Int. Cl.

| | |
|---|---|
| ***A61C 13/083*** | (2006.01) |
| ***A61K 6/833*** | (2020.01) |
| ***C03B 19/10*** | (2006.01) |
| ***C03B 32/02*** | (2006.01) |
| ***C03C 4/00*** | (2006.01) |

(52) U.S. Cl.

CPC .......... *A61K 6/833* (2020.01); *C03B 19/1045* (2013.01); *C03B 32/02* (2013.01); *C03C 4/0021* (2013.01)

(56) References Cited

FOREIGN PATENT DOCUMENTS

| | | | |
|---|---|---|---|
| CN | 106277798 | A | 1/2017 |
| CN | 113264684 | * | 8/2021 |
| CN | 113264684 | A | 8/2021 |
| CN | 114907015 | A | 8/2022 |
| CN | 115028364 | A | 9/2022 |
| DE | 102005028637 | A1 | 12/2006 |
| DE | 10362378 | B3 | 1/2014 |

OTHER PUBLICATIONS

European Search Report issued in counterpart European Patent Application No. EP 23202504.9, dated Mar. 13, 2024.

First Office Action issued in counterpart Chinese Patent Application No. 202211280088.8, dated Apr. 13, 2024.

* cited by examiner

GLASS CERAMIC MATERIAL, METHOD FOR PREPARING THE SAME, AND DENTURE

CROSS-REFERENCE TO RELATED APPLICATIONS

This application claims priority to Chinese Patent Application No. 202211280088.8, filed on Oct. 19, 2022, the entire contents of which are incorporated herein by reference.

TECHNICAL FIELD

The present application relates to the technical field of materials, and in particular, to a glass ceramic material, a method for preparing the same, and a denture.

BACKGROUND

Lithium disilicate glass ceramics are widely used in the field of dental restoration due to their excellent mechanical properties and outstanding aesthetic effects. At present, it is mainly applied to veneers, dental bridges, crowns, inlays, implant abutments, etc. Due to the high strength of the lithium disilicate glass ceramics, it is difficult to process and grind them by using CAD/CAM, which seriously affects the service life of the bur. In the industry, a matrix glass is often crystallized to generate a lithium metasilicate glass ceramic, then is molded and processed, finally the formed lithium metasilicate glass ceramic is heat treated to obtain a lithium disilicate glass ceramic. Since the strength of the lithium metasilicate glass ceramic is lower than that of the lithium disilicate glass ceramic, molding and processing are relatively easy.

In actual production, due to the accompanying formation of lithium metasilicate and lithium disilicate, uncontrollable formation of lithium disilicate can lead to an increase in the strength of the glass ceramic, which often causes the bur to break and affect grinding efficiency, thereby increasing processing costs. In order to avoid this situation, manufacturers in the industry often produce the lithium metasilicate glass ceramic with low crystallinity by decreasing the crystallization temperature. Although the glass ceramic with low crystallinity can reduce the strength and facilitate grinding, their products have poor toughness due to the high proportion of glass phase, and their edges are prone to cracking when veneers or crowns is processed. In order to solve this problem, some manufacturers in the industry increase the zirconium content in the matrix glass to improve the toughness. However, a small zirconium content is difficult to enhance the toughness. Although a higher zirconium content (mass ratio >10%) can enhance the toughness and improve grinding performance, its requirements for glass melting are too high, and the costs is high. On the other hand, zirconia has a high density and difficult to melt, which often leads to zirconium deposition and affects the uniformity of the product.

Therefore, the existing glass-ceramic material has the problem that the edges are easy to crack during grinding.

SUMMARY

The purpose of the present application is to provide a glass ceramic material, aiming at solving the problem that the edge of the existing glass ceramic material is easy to crack during grinding.

The present application provides a glass ceramic material, including the following components by mass percentage:

58% to 72% of $SiO_2$, 0% to 4% of $Al_2O_3$, 0% to 5% of $Na_2O$, 3% to 8% of $K_2O$, 8% to 17% of $Li_2O$, 2.5% to 5% of $P_2O_5$, 0% to 2% of MgO, 0% to 2.5% of $B_2O_3$, 0% to 5% of ZnO and 0% to 3% of $ZrO_2$;

a total mass percentage of $SiO_2$, $Al_2O_3$ and $ZrO_2$ is greater than that of $R_2O$ and a difference between them is 30% to 60%, and $R_2O$ is a sum of the mass percentage of $Na_2O$, $K_2O$ and $Li_2O$;

a ratio of the mass percentage of $SiO_2$ to a total mass percentage of $Li_2O$ and $P_2O_5$ is 2% to 6%, the mass percentage of $Li_2O$ is greater than that of $P_2O_5$ and a difference between them is 7% to 13.5%, and a ratio of a total mass percentage of $ZrO_2$, ZnO, $Na_2O$ and $Al_2O_3$ to the mass percentage of $Li_2O$ is 0.2% to 0.8%.

The present application also provides a method for preparing the glass ceramic material, including:

weighing raw materials according to the formula of the glass ceramic material, high-temperature melting the raw materials, and performing wet ball milling treatment after water quenching to obtain a mixed powder;

drying and dry-pressing molding the mixed powder to obtain a first green body;

vacuum-packaging the first green body and performing a warm isostatic pressing treatment to obtain a second green body; and subjecting the second green body to a crystallization heat treatment to obtain a glass ceramic material for dental use.

The present application also provides a denture, and the denture is obtained by sintering a glass ceramic material that is prepared by the glass ceramic material or the method for preparing the glass ceramic material.

In the embodiments of the present application, through rational designing the composition and proportion of the glass ceramic material and combining with the matching process conditions, it is possible to prepare the glass ceramic material whose crystal phase is lithium metasilicate, the crystallinity is greater than 50% and the hardness is 500 $kgf/mm^2$ to 590 $kgf/mm^2$. The glass ceramic material does not need to introduce a high proportion of zirconia content, and can be ground to a thickness of 0.2 mm without edge collapse. In addition, it is possible to prepare a glass ceramic denture product by secondary sintering, the crystal phase of which is lithium disilicate, the crystallinity is greater than 80%, flexural strength is greater than 400 MPa, and fracture toughness is greater than 2.5 $Mpa \cdot m^{1/2}$. The product of the present application has a short holding time for heat treatment, high grinding efficiency, less damage to the bur, and less edge collapse of the product. It has a very competitive advantage and has a great application prospect.

DETAILED DESCRIPTION OF THE EMBODIMENTS

Figure 1:
FIG. 1 is a morphological picture of a sample before secondary sintering according to Embodiment 2 of the present application.

In order to make the purpose, technical solution and advantages of the present application clearer, the present application will be further described in detail below in conjunction with the accompanying drawings and embodiments. It should be understood that the specific embodiments described here are only used to explain the present application, and are not intended to limit the present application.

In order to solve the problem that the edge of the existing glass-ceramic material is easy to crack during grinding, the present application provides a glass-ceramic material. The present application optimizes the composition and the ratio of the glass-ceramic material and combines the matching process, it is possible to control the formation of lithium disilicate while the crystallinity of the lithium metasilicate glass ceramic can be increased without introduction of a high ration of zirconia content, thereby improving the grinding performance of the glass ceramic.

In the embodiment of the present application, the glass ceramic material includes the following components by mass percentage: 58% to 72% of $SiO_2$, 0% to 4% of $Al_2O_3$, 0% to 5% of $Na_2O$, 3% to 8% of $K_2O$, 8% to 17% of $Li_2O$, 2.5% to 5% of $P_2O_5$, 0% to 2% of MgO, 0% to 2.5% of $B_2O_3$, 0% to 5% of ZnO and 0% to 3% of $ZrO_2$.

The components also need to satisfy the following conditions: a total mass percentage of $SiO_2$, $Al_2O_3$ and $ZrO_2$ is greater than that of $R_2O$ and a difference between them is 30% to 60%, where $R_2O$ is a sum of the mass percentage of $Na_2O$, $K_2O$ and $Li_2O$; a ratio of the mass percentage of $SiO_2$ to a total mass percentage of $Li_2O$ and $P_2O_5$ is 2% to 6%; the mass percentage of $Li_2O$ is greater than that of $P_2O_5$ and a difference between them is 7% to 13.5%; and a ratio of a total mass percentage of $ZrO_2$, ZnO, $Na_2O$ and $Al_2O_3$ to the mass percentage of $Li_2O$ is 0.2% to 0.8%.

Further, in order to make the color of the glass ceramic material similar to that of natural teeth, the glass ceramic material also needs to introduce colorants and fluorescent agents, which are mainly one or a combination of more of $TiO_2$, $La_2O_3$, $V_2O_5$, $CeO_2$, $Er_2O_3$, $Y_2O_3$, $Nd_2O_3$, $Pr_2O_3$, $Mn_2O_3$, NiO, and $Fe_2O_3$, and the total content is 1% to 6%.

In the glass ceramic material of the present application, $SiO_2$ is the main network forming agent, which can stabilize the network structure, constitute the main structure of the glass ceramic, and is also the main component of the crystal phase. If its content is too low, it can lead to changes in the types of crystal phases, and also weaken the overall performance of the glass ceramic. The content of $SiO_2$ should not be lower than 58 wt %. However, a higher content of $SiO_2$ can lead to difficulty in melting and forming, and the crystal phase can also form a solid solution of $SiO_2$. Therefore, based on comprehensive consideration, the present application controls the content of $SiO_2$ to be 58 wt % to 72 wt %.

In some embodiments, $Al_2O_3$ is contained, which has a certain effect on the permeability adjustment of the glass ceramic. The higher the content, the better the permeability. However, $Al_2O_3$ is an extremely refractory oxide, which can quickly increase the high-temperature viscosity of the glass and make it more difficult to clarify and homogenize the glass. The bubble defects are not easy to discharge, therefore the content of $Al_2O_3$ is controlled to be less than 4%.

In some embodiments, the glass ceramic precursor contains alkali metal oxides $R_2O$, which are mainly $Na_2O$, $K_2O$ and $Li_2O$; wherein $Na_2O$ is mainly used to reduce the viscosity of the glass ceramic melt and promote the melting and clarification of the precursor. However, excessive content of $Na_2O$ can increase coefficient of thermal expansion (CTE) and lead to changes in mechanical properties. Therefore, the present application controls the content of $Na_2O$ to 0% to 5%.

In some embodiments, $K_2O$ is beneficial to enhance the gloss of the glass ceramic, and its content is not less than 3%. Not limited to theory, it is found through experiments in the present application that a higher content of $K_2O$ can inhibit the formation of lithium disilicate during secondary sintering, which is not conducive to the final conversion of lithium metasilicate, resulting in a decrease in the performance of dental products. Therefore, the content of $K_2O$ is controlled to be 3% to 8%.

In some embodiments, $Li_2O$ is the main component of the crystal phase. When the content of $Li_2O$ is too low, the crystal phase cannot be formed, and the minimum content needs to be greater than 8%. However, too high content of $Li_2O$ can cause uncontrolled crystallization, leading to glass crystallization during molding, thereby resulting in defects and affecting subsequent processes.

In some embodiments, $P_2O_5$ can reduce the activated energy of nucleation, facilitate the crystallization of glass, and serve as a nucleating agent for the glass ceramic. If the content of $P_2O_5$ is too low, the glass is difficult to crystallize. The content of $P_2O_5$ is at least 2.5 wt %. However, if the content of $P_2O_5$ is too high, the phase separation of the glass can be severe, which can affect the permeability of the glass ceramic. The content of $P_2O_5$ is at most 5 wt %.

In some embodiments, alkaline earth metal oxide RO is contained, and $R^{2+}$ is $Mg^{2+}$ and $Zn^{2+}$, which can improve the chemical stability and mechanical strength of the glass. In the present application, the content of MgO is limited to be 0% to 2% and ZnO to be 0% to 5%.

In some embodiments, $B_2O_3$ is a network former oxide, which can reduce the high-temperature melting viscosity of the glass, improve the melting characteristics, and facilitate the homogenization of glass components at high temperature. However, a high content of $B_2O_3$ can easily lead to phase separation and defects in the glass. Therefore, the present application controls the mass percentage of $B_2O_3$ to be 0% to 2.5%.

It is noted that, according to the present application, when the total mass percentage of $SiO_2$, $Al_2O_3$ and $ZrO_2$ is greater than the mass percentage of $R_2O$ in the composition and the difference between them is lower than 30%, the overall viscosity of the glass body is low, which provides an extremely convenient flow environment for the movement of crystalline protons, making it difficult to control the crystallization process, affecting the uniformity of crystallization, and also making it easier to convert lithium metasilicate into lithium disilicate. When the above difference between the total mass percentage of $SiO_2$, $Al_2O_3$ and $ZrO_2$ and the mass percentage of $R_2O$ is greater than 60%, the overall viscosity becomes larger, and the overall temperature required the crystalline material rises. In order to match the rapid sintering furnace of a denture factory or hospital, it is necessary to ensure that the secondary sintering temperature is controlled below 900° C. Therefore, the above difference between the total mass percentage of $SiO_2$, $Al_2O_3$ and $ZrO_2$ and the mass percentage of $R_2O$ is controlled to be 30% to 60%.

In addition, in order to maximize the control of the crystallinity of lithium metasilicate, it is necessary to ensure that the ratio of the mass of $SiO_2$ to the total mass of $Li_2O$ and $P_2O_5$ is 2% to 6%; when the ratio is too low, excessive $Li_2O$ and $P_2O_5$ in the composition can induce the direct generation of lithium disilicate, resulting in a small proportion of the crystal phase of lithium metasilicate; when the ratio is too high, the excessive $SiO_2$ can form a solid solution of $SiO_2$ during the secondary sintering (T>800° C.), resulting in an increase in the crystal phase of the final product and affecting the final performance.

Similarly, in order to avoid the formation of $Li_3PO_4$ crystal phase during the secondary sintering, resulting in an increase in the crystal phase of the final product, the mass percentage of $Li_2O$ is greater than the mass percentage of $P_2O_5$ and the difference between them is limited to be 7% to 13.5%.

Since dental products have requirements on the final transmittance of the teeth, a higher transmittance appears too bright and unreal, while a too low transmittance appears burnt and lack luster. For this reason, the ratio of the total mass of $ZrO_2$, ZnO, $Na_2O$ and $Al_2O_3$ to the mass of $Li_2O$ is limited to be 0.2% to 0.8%.

Figure 4:
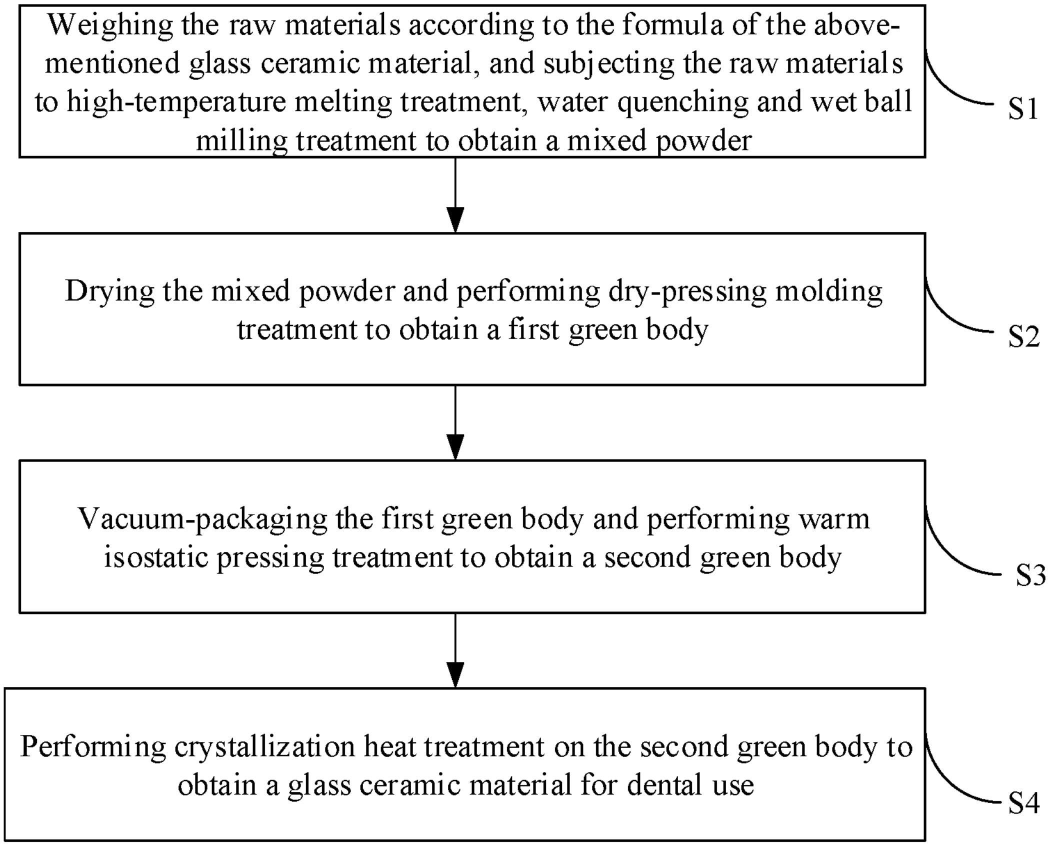
FIG. 4 is a flowchart showing a method for preparing the sample according to the present application.

The present application also provides a method for preparing a glass ceramic material, as shown in FIG. 4, including the following steps.

Step S1, weighing the raw materials according to the formula of the above-mentioned glass ceramic material, and subjecting the raw materials to high-temperature melting treatment, water quenching and wet ball milling treatment to obtain a mixed powder.

In the embodiment of the present application, the glass ceramic composition is melted at a high temperature of 1400° C. to 1600° C. After the melting is completed, water quenching is carried out. After water quenching, wet ball milling is carried out for 30 min to 100 min, and a particle size is controlled to be 5 μm to 20 μm.

Step S2, drying the mixed powder and performing dry-pressing molding treatment to obtain a first green body.

In the embodiment of the present application, the powder after ball-milling is dried at a drying temperature of 100° C. to 200° C.; the powder after drying is subjected to dry-pressing molding at a molding pressure of 5 MPa to 30 MPa and a holding time of 10 s to 60 s.

Step S3, vacuum-packaging the first green body and performing warm isostatic pressing treatment to obtain a second green body.

In the embodiment of the present application, the green body after the dry-pressing molding treatment is vacuum-packaged; after vacuum-packaged, the green body is subjected to the warm isostatic pressing treatment at a pressure of 100 MPa to 200 MPa, a temperature of 50° C. to 150° C., and a holding time of 6 min to 20 min.

Step S4, performing crystallization heat treatment on the second green body to obtain a glass ceramic material for dental use.

In the embodiment of the present application, the green body after the warm isostatic pressing is subjected to crystallization heat treatment. The method is as follows: putting the glass ceramic composition sample after warm isostatic pressing into a crystallization furnace, heating to a nucleation temperature range of 500° C. to 570° C. at a heating rate of 3° C./min to 10° C./min, and keeping for 5 min to 30 min; heating to a crystallization temperature at a heating rate of 3° C./min to 5° C./min, wherein the optimum crystallization temperature is controlled at 700° C. to 730° C., and a holding time is 5 min to 20 min; and taking it out after cooling down in the furnace to obtain the glass ceramic material.

The crystalline phase of the glass ceramic material according to the present application is lithium metasilicate, with a crystallinity greater than 50%; the crystal grains are granular, with an average size of 30 nm to 60 nm; the hardness is 500 kgf/mm$^2$ to 590 kgf/mm$^2$; it can be ground to a thickness of 0.2 mm without edge collapse. After ground, the glass ceramic material can be kept in a rapid sintering furnace at 830° C. to 850° C. for 5 min to 10 min to complete the sintering of the denture; after secondary sintering, a flexural strength is greater than 400 MPa; a fracture toughness is greater than 2.5 Mpa·m$^{1/2}$; the crystal phase is plate-like interlocking lithium disilicate, with the crystallinity greater than 80%.

Examples of some embodiments of the present application are given below, which are not intended to limit the scope of the present application.

In addition, it should be noted that values given in the following examples are as accurate as possible, but those skilled in the art can understand that each of the values should be understood as a divisor rather than an absolutely accurate value due to unavoidable measurement errors and experimental operation problems.

Embodiments 1 to 8 of the Present Application are Prepared by the Following Method First, weighing and mixing the oxides of each component in proportion evenly, putting the uniform mixture into a crucible made of platinum or platinum rhodium, and melting it in an electric furnace at a temperature of 1500° C. for 3 h. After melting, water quenching is carried out, after water quenching, wet ball milling is carried out for 50 min, where the particle size is controlled at 10 μm. After ball milling, drying is carried out at the drying temperature of 150° C.; the powder after drying is dry-pressing molded, with a forming pressure of 15 MPa and the holding time of 30s; the green body after dry-pressing molded is vacuum-packed, after vacuum-packed, the green body is subjected to the warm isostatic pressing treatment, with a pressure of 150 MPa, a temperature of 100° C. and the holding time of 10 min. Crystallization heat treatment is carried out on the green body after the warm isostatic pressing treatment, specifically: putting the green body after the warm isostatic pressing treatment into the crystallization furnace, heating to the nucleation temperature at the heating rate of 6° C./min and keeping for a period of time, and heating to the crystallization temperature at the heating rate of 4° C./min and keeping for a period of time; and taking it out after cooling down in the furnace to obtain the glass ceramic material. After bonded to a handle, the glass ceramic material is ground and processed to produce various dental repair materials, then is placed in the rapid sintering furnace, and is subjected to secondary sintering to prepare the glass ceramic denture of different colors. The nucleation process parameters, crystallization process parameters and secondary sintering process parameters corresponding to Embodiments 1-8 are shown in Table 1. The formula components corresponding to Embodiments 1-8 are shown in Table 2.

TABLE 1

| heat treatment process | Embodiment 1 | Embodiment 2 | Embodiment 3 | Embodiment 4 | Embodiment 5 | Embodiment 6 | Embodiment 7 | Embodiment 8 |
|---|---|---|---|---|---|---|---|---|
| nucleation temperature (° C.) | 520 | 550 | 560 | 530 | 510 | 520 | 550 | 570 |
| nucleation time (min) | 10 | 20 | 20 | 10 | 30 | 25 | 10 | 5 |
| crystallization temperature (° C.) | 700 | 720 | 720 | 710 | 730 | 710 | 730 | 700 |
| crystallization time (min) | 20 | 10 | 10 | 20 | 5 | 10 | 10 | 10 |
| secondary sintering temperature (° C.) | | | | 840 | | | | |
| secondary sintering time (min) | | | | 5 | | | | |

TABLE 2

| oxide (wt %) | Embodiment 1 | Embodiment 2 | Embodiment 3 | Embodiment 4 | Embodiment 5 | Embodiment 6 | Embodiment 7 | Embodiment 8 |
|---|---|---|---|---|---|---|---|---|
| $SiO_2$ | 68.00 | 59.00 | 70.00 | 71.20 | 67.20 | 62.56 | 69.77 | 67.75 |
| $Al_2O_3$ | 2.05 | 2.90 | 0.00 | 3.20 | 1.92 | 3.78 | 1.56 | 2.25 |
| $Na_2O$ | 0.80 | 2.20 | 3.80 | 0.50 | 3.20 | 2.54 | 0.00 | 0.30 |
| $K_2O$ | 3.60 | 5.80 | 3.50 | 6.48 | 4.80 | 3.10 | 4.41 | 3.70 |
| $Li_2O$ | 12.30 | 15.25 | 13.78 | 10.25 | 14.15 | 15.23 | 16.20 | 15.50 |
| $P_2O_5$ | 3.00 | 4.55 | 3.15 | 2.80 | 4.50 | 3.70 | 3.10 | 3.00 |
| $ZrO_2$ | 1.22 | 2.10 | 0.23 | 0.00 | 1.10 | 0.85 | 0.90 | 2.50 |
| $B_2O_3$ | 0.50 | 0.50 | 1.00 | 0.00 | 0.20 | 0.00 | 0.20 | 0.20 |
| MgO | 0.20 | 0.10 | 0.37 | 0.00 | 0.18 | 0.68 | 0.00 | 0.00 |
| ZnO | 2.88 | 3.33 | 2.05 | 2.11 | 1.74 | 4.50 | 1.85 | 2.25 |
| $TiO_2$ | 0.70 | 0.00 | 0.00 | 0.30 | 0.00 | 0.45 | 0.00 | 0.50 |
| $V_2O_5$ | 1.70 | 2.00 | 0.50 | 0.80 | 0.30 | 0.15 | 0.30 | 0.25 |
| $CeO_2$ | 2.77 | 1.50 | 1.35 | 2.10 | 1.85 | 2.20 | 1.25 | 1.55 |
| $Er_2O_3$ | 0.20 | 0.60 | 0.15 | 0.22 | 0.33 | 0.00 | 0.00 | 0.18 |
| $Y_2O_3$ | 0.00 | 0.00 | 0.02 | 0.03 | 0.00 | 0.01 | 0.00 | 0.00 |
| $Nd_2O_3$ | 0.00 | 0.00 | 0.00 | 0.01 | 0.00 | 0.00 | 0.00 | 0.00 |
| $La_2O_3$ | 0.00 | 0.00 | 0.10 | 0.00 | 0.15 | 0.00 | 0.00 | 0.00 |
| $Mn_2O_3$ | 0.00 | 0.05 | 0.00 | 0.00 | 0.00 | 0.00 | 0.05 | 0.05 |
| NiO | 0.00 | 0.02 | 0.00 | 0.00 | 0.01 | 0.00 | 0.00 | 0.00 |
| $Fe_2O_3$ | 0.03 | 0.00 | 0.00 | 0.00 | 0.00 | 0.25 | 0.41 | 0.02 |
| $Pr_2O_3$ | 0.05 | 0.10 | 0.00 | 0.00 | 0.80 | 0.00 | 0.00 | 0.00 |
| $(SiO_2 + Al_2O_3 + ZrO_2)—R_2O$ | 54.57 | 40.75 | 49.15 | 57.17 | 48.07 | 46.32 | 51.62 | 53.00 |
| $SiO_2/(Li_2O + P_2O_5)$ | 4.44 | 2.98 | 4.13 | 5.46 | 3.60 | 3.30 | 3.62 | 3.66 |
| $Li_2O—P_2O_5$ | 9.30 | 10.70 | 10.63 | 7.45 | 9.65 | 11.53 | 13.10 | 12.50 |
| content of colorant | 5.45 | 4.27 | 2.12 | 3.46 | 3.44 | 3.06 | 2.01 | 2.55 |
| $(ZrO_2 + ZnO + Na_2O + Al_2O_3)/Li_2O$ | 0.57 | 0.69 | 0.44 | 0.57 | 0.56 | 0.77 | 0.27 | 0.47 |

The grain sizes, the crystal phase content, hardness and grinding effect of the glass ceramic materials as well as the crystal phase content, flexural strength and fracture toughness of the glass ceramic denture prepared in embodiments 1 to 8 were tested, and the results are shown in Table 3.

Average grain size is measured by scanning electron microscope (SEM), performing a surface scanning using the SEM, observing the diameter of the particles, summing up the average diameter of all grain sections and divided by the number of grains in the SEM image. The crystal phase is determined by comparing XRD diffraction peaks with the database spectrum to determine, and the proportion of diffraction intensity of the crystal phase in the overall spectrum intensity is calculated by Rietveld method to obtain the crystallinity and amorphous content. Vickers hardness is measured by Vickers hardness tester, with a loading force of 200 g, and a loading time is 10 s. Grinding effect is measured using an intelligent tooth carving machine. Flexural strength was tested using a universal testing machine. Fracture toughness was tested using a universal testing machine for four-point bending testing.

TABLE 3

| | Embodiment 1 | Embodiment 2 | Embodiment 3 | Embodiment 4 | Embodiment 5 | Embodiment 6 | Embodiment 7 | Embodiment 8 |
|---|---|---|---|---|---|---|---|---|
| crystal phase | lithium metasilicate | | | | | | | |
| crystallinity | >50% | | | | | | | |
| grain size (nm) | 42 | 48 | 45 | 50 | 50 | 46 | 55 | 32 |
| hardness (kgf/mm$^2$) | 510 | 522 | 514 | 578 | 565 | 570 | 582 | 550 |
| grinding effect (mm) | 0.2, no edge collapse | | | | | | | |
| flexural strength after secondary sintering (MPa) | 451 | 482 | 415 | 423 | 464 | 428 | 469 | 488 |
| fracture toughness after secondary sintering (2 Mpa · m$^{1/2}$) | 2.6 | 2.7 | 2.8 | 2.8 | 2.6 | 2.5 | 2.7 | 2.8 |
| crystallinity after secondary sintering | >80% | | | | | | | |

Figure 2:
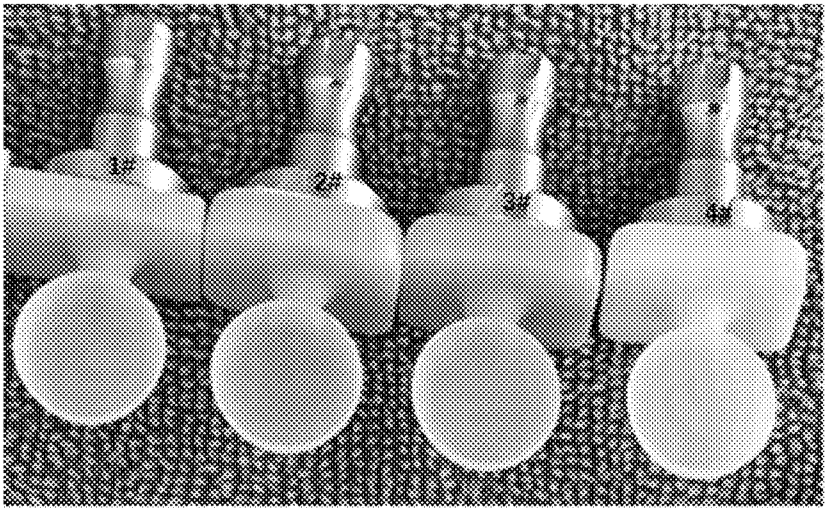
FIG. 2 is a grinding effect picture of the sample before secondary sintering according to Embodiments 1 to 4 of the present application.
Figure 3:
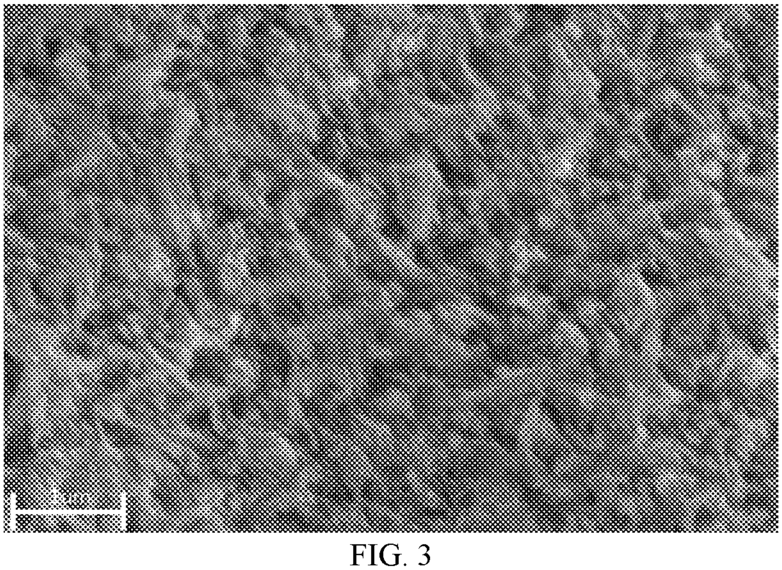
FIG. 3 is a morphological picture of the sample after secondary sintering according to Embodiment 3 of the present application.

In addition, the morphology of the samples prepared in embodiments 1 to 4 of the present application was observed, as shown in FIG. 1 to FIG. 3. FIG. 1 is a scanning electron microscope (SEM) image of the samples before secondary sintering according to embodiment 2 of the present application, with the average grain size of 30 nm to 60 nm, FIG. 2 shows the grinding effect of the samples before secondary sintering according to embodiments 1 to 4 of the present application, with an edge wall thickness of 0.2 mm, and FIG. 3 is the SEM image of the samples after being kept in a rapid sintering furnace at 840° C. for 5 min according to embodiment 3 of the present application, and the samples have a plate-like crystal form.

To sum up, in the embodiments of the present application, by optimizing the composition and ratio of the glass ceramic material, and controlling the nucleation temperature at 500° C. to 570° C. and the crystallization temperature at 700° C. to 730° C., it is possible to prepare lithium metasilicate glass ceramic with the crystallinity greater than 50%, grain size of 30 nm to 60 nm and hardness of 500 kgf/mm$^2$ to 590 kgf/mm$^2$. The lithium metasilicate glass ceramic does not need to introduce high proportion of zirconia content in the composition, and can be ground to a thickness of 0.2 mm without edge collapse. The lithium metasilicate glass ceramic is kept in the rapid sintering furnace at 830° C. to 850° C. for 5 min to 10 min, and it is possible to prepare a glass ceramic denture product with the crystal phase of lithium disilicate, crystallinity greater than 80%, flexural strength greater than 400 MPa and fracture toughness greater than 2.5 Mpa·m$^{1/2}$. The product of the present application has a short holding time for heat treatment, high grinding efficiency, less damage to the bur, and less edge collapse of the product. It has a very competitive advantage and has a great application prospect.

The above-mentioned embodiments only describe several implementation modes of the present application, and the description thereof is relatively specific and detailed, but cannot be construed as limiting the scope of the present application. It should be noted that those skilled in the art can make several modifications and improvements without departing from the concept of the present application, all of which shall fall within the scope of the present application. Therefore, the scope of the present application should be based on the appended claims.

The above descriptions are only preferred embodiments of the present application, and are not intended to limit the present application. Any modifications, equivalent replacements and improvements made within the spirit and principles of the present application should be included in the scope of the present application.

What is claimed is:

1. A method for preparing a lithium silicate based glass ceramic material, wherein the lithium silicate based glass ceramic material comprises the following components by mass percentage:

58% to 72% of $SiO_2$, 0% to 4% of $Al_2O_3$, 0% to 5% of $Na_2O$, 3% to 8% of $K_2O$, 8% to 17% of $Li_2O$, 2.5% to 5% of $P_2O_5$, 0% to 2% of MgO, 0% to 2.5% of $B_2O_3$, 0% to 5% of ZnO and 0% to 3% of $ZrO_2$;

wherein a total mass percentage of $SiO_2$, $Al_2O_3$ and $ZrO_2$ is greater than that of $R_2O$ and a difference between them is 30% to 60%, and $R_2O$ is a sum of the mass percentage of $Na_2O$, $K_2O$ and $Li_2O$;

a ratio of the mass percentage of $SiO_2$ to a total mass percentage of $Li_2O$ and $P_2O_5$ is 2% to 6%, the mass percentage of $Li_2O$ is greater than that of $P_2O_5$ and a difference between them is 7% to 13.5%, and a ratio of a total mass percentage of $ZrO_2$, ZnO, $Na_2O$ and $Al_2O_3$ to the mass percentage of $Li_2O$ is 0.2% to 0.8%;

the method comprising:

weighing raw materials according to a formula of the lithium silicate based glass ceramic material, high-temperature melting the raw materials, and performing wet ball milling treatment after water quenching to obtain a mixed powder;

drying and dry-pressing molding the mixed powder to obtain a first green body;

vacuum-packaging the first green body and performing a warm isostatic pressing treatment to obtain a second green body, wherein process conditions for the warm isostatic pressing treatment are a pressure of 100 MPa to 200 MPa, a temperature of 50° C. to 150° C. and a holding time of 6 min to 20 min; and subjecting the second green body to a crystallization heat treatment to obtain a glass ceramic material for dental use.

2. The method for preparing the lithium silicate based glass ceramic material according to claim 1, wherein a temperature for the high-temperature melting is 1400° C. to 1600° C.

3. The method for preparing the lithium silicate based glass ceramic material according to claim 1, wherein process conditions for the dry-pressing molding are a molding pressure of 5 MPa to 30 MPa and a holding time of 10 s to 60 s.

4. The method for preparing the lithium silicate based glass ceramic material according to claim 1, wherein subjecting the second green body to the crystallization heat treatment to obtain the glass ceramic material for dental use comprises:

putting the second green body into a crystallization furnace, heating up to a nucleation temperature of 500° C. to 570° C. at a heating rate of 3° C./min to 10° C./min, and keeping for 5 min to 30 min; heating up to a crystallization temperature of 700° C. to 730° C. at a heating rate of 3° C./min to 5° C./min, keeping for 5 min to 20 min; and taking the second green body out after cooling down in the furnace to obtain the glass ceramic material for dental use.

5. A denture, obtained by sintering a glass ceramic material that is prepared by the method for preparing the lithium silicate based glass ceramic material according to claim 1.

6. The denture according to claim 5, wherein process conditions for the sintering treatment are a temperature of 830° C. to 850° C. and a holding time of 5 min to 10 min.

* * * * *